US005760213A

United States Patent [19]
Ooiso et al.

[11] Patent Number: 5,760,213
[45] Date of Patent: Jun. 2, 1998

[54] IMMUNOACTIVATING AGENT

[75] Inventors: Yoichi Ooiso, Higashiosaka; Ryosuke Sugihara, Osaka; Hitoshi Oomori, Okayama, all of Japan

[73] Assignee: Tayca Corporation, Osaka-fu, Japan

[21] Appl. No.: 793,144

[22] PCT Filed: Jun. 5, 1996

[86] PCT No.: PCT/JP96/01519

§ 371 Date: Apr. 14, 1997

§ 102(e) Date: Apr. 14, 1997

[87] PCT Pub. No.: WO96/39155

PCT Pub. Date: Dec. 12, 1996

[30] Foreign Application Priority Data

Jun. 5, 1995 [JP] Japan .................... 7-162842

[51] Int. Cl.$^6$ ...................................... C07H 3/00
[52] U.S. Cl. ........................... 536/123.1; 514/54
[58] Field of Search ................. 536/1.11, 123, 536/123.1; 514/23, 54

[56] References Cited

U.S. PATENT DOCUMENTS 5,476,656  12/1995  Kawaguchi et al. ............... 424/116

*Primary Examiner*—Elli Peselev
*Attorney, Agent, or Firm*—David G. Conlin; George W. Neuner

[57] ABSTRACT

An immunoactivating agent comprising a polysaccharide consisting essentially of glucuronic acid, rhamnose, galactose and glucose in a molar ratio of glucuronic acid:rhamnose:galactose:glucose=0 to 1.2:2.4 to 3.6:0.8 to 1.2:0.8 to 2.4. This immunoactivating agent has an excellent immunoactivating activity, and the polysaccharide is a microbially produced acidic heteropolysaccharide having higher productivity than the basidiomycete-derived polysaccharides such as krestin and lentinan.

6 Claims, No Drawings

IMMUNOACTIVATING AGENT

FIELD OF THE ART

The present invention relates to an immunoactivating agent, and more particularly relates to an immunoactivating agent comprising a microbially produced polysaccharide.

BACKGROUND ART

Chemical therapy is exemplified as a method for cancer treatment, but the chemical therapeutical agents used therefor usually have high toxicity and tend to produce unfavorable side effects. Under these circumstances, attention is attracted to the idea of preventing and treating cancer as well as bacterial and viral infections by enhancing immunity possessed by the organism itself, and it is desired to provide a substance having an immunoactivating function.

A variety of polysaccharides have been utilized in the fields of medicines, foods and cosmetics. Natural polysaccharides may be roughly classified into the following three types: plant-derived polysaccharides, animal-derived polysaccharides and microorganism-derived polysaccharides. Among them, the polysaccharides derived from microorganisms (microbially produced polysaccharides) have come to be used popularly for convenience of production and supply.

β-1,3 glucans such as lentinan and krestin have been known as polysaccharides utilized for immunoactivating agent (Japanese Patent Publication (KOKOKU)) Nos. 55-12886, 56-46481, etc.). These polysaccharides are obtained as products by basidiomycetes, so that as compared with the polysaccharides produced by microorganisms, their productivity is not sufficient high, with the yield being usually less than 10% based on the cells. As an instance of acidic heteropolysaccharides having an immunoactivating activity, there is known a polysaccharic substance A29-PS disclosed in Japanese Patent Publication (KOKOKU) No. 1-59283, but its effect is not satisfactory.

The present invention has been made in view of the above circumstances, and its object is to provide an immunoactivating agent comprising a polysaccharide produced by a microorganism. As a result of the present inventors' earnest studies, it has been found that the polysaccharides produced by the bacteria of the genus Klebsiella have excellent immunoactivating activity and can be obtained with higher productivity than the basidiomycetes-produced polysaccharides such as lentinan and krestin, and have reached the present invention.

DISCLOSURE OF THE INVENTION

Thus, the aspect of the present invention lies in an immunoactivating agent comprising a polysaccharide consisting essentially of four types of saccharides, viz. glucuronic acid, rhamnose, galactose and glucose, and having a molar ratio of glucuronic acid:rhamnose:galactose:glucose of 0 to 1.2:2.4 to 3.6:0.8 to 1.2:0.8 to 2.4.

Hereinbelow the present invention is described in detail.

In the polysaccharide used for the immunoactivating agent of the present invention, usually glucuronic acid, galactose and glucose are D-form and rhamnose is L-form. The polysaccharides used in the present invention preferably have the following characteristics besides the features mentioned above.

(1) Composition

The preferable molar ratio of the constituting sugars is glucuronic acid:rhamnose:galactose:glucose=0.8 to 1.2:2.4 to 3.6:0.8 to 1.2:0.8 to 1.2.

(2) Molecular weight

The molecular weight of the polysaccharide as measured by gel filtration chromatography is in the range of approximately $1 \times 10^3$ to $10 \times 10^6$.

(3) Bonding forms

The bonding form of L-rhamnose is (1→2) bond and (1→bond). (The constituting ratios of the above bonding forms are (1→2):(1→bond)=1.3 to 3.0:1.)

The bonding form of D-glucuronic acid is (1→3) bond and (1→4) bond.

The bonding form of D-galactose is (1→3) bond.

The bonding form of D-glucose is (1→2) bond.

(4) Bonding configuration

The bonding configuration of L-rhamnose, D-glucuronic acid and D-glucose is α, and the bonding configuration of D-galactose is β.

(5) Main bonding forms and molar ratio of constituting sugars

= 0.8 to 1.2:1.6 to 2.4:0.8 to 1.2:0.8 to 1.2:0.8 to 1.2.

(wherein Rha, Gal, Glc and GlcUA represent rhamnose residue, galactose residue, glucose residue and glucuronic acid residue, respectively, and the numerical figures indicate the position of the glycoside bond).

(6) Main bonding forms and molar ratio of the constituting sugars in case where the carboxyl group in the glucuronic acid was reduced

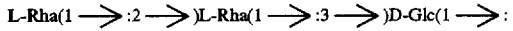

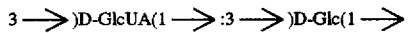

= 0.8 to 1.2:1.6 to 2.4:0.8 to 1.2:0.8 to 1.2:0.8 to 2.4.

The polysaccharides in the present invention have the following properties.

(7) Form

White fibrous (freeze-dried).

(8) Solubility

Soluble in water, dilute acids and dilute alkalis, and insoluble in methanol, ethanol and acetone.

(9) Infra-red (IR) absorption spectrum

IR absorption peaks are observed at around 3400 cm$^{-1}$, around 1620 cm$^{-1}$, around 1100 cm$^{-1}$, around 1250 cm$^{-1}$ and around 2950 cm$^{-1}$.

(10) Color reaction

Positive for phenolsulfuric acid reaction, carbazolesulfuric acid reaction and m-phenylphenol reaction.

The molecular weight of the polysaccharide in the present invention, the kind, compositional ratios and bonding forms of the component saccharides can be specified by chromatographical analysis, methylation or Smith's decomposition after acid hydrolysis. An example of the specifying methods is shown below.

<Determination of molecular weight>

Molecular weight was determined by GPC-mode high-performance liquid chromatography with a column of "Asahipak GFA-7MF" (mfd. by Asahi Chemical Industry Co., Ltd.) using a molecular weight-retention time standard curve drawn up with pullulan of the known molecular weight as standard sample and with a 0.1M $NaNO_3$ solution as mobile phase.

<Component saccharides and their ratios>

The above polysaccharide and the modified one in which the carboxyl group of the uronic acid residue had been reduced were subjected to acid hydrolysis using 2M trifluoroacetic acid (TFA) at 100° C. for 6 hours to prepare the corresponding alditol acetates. Each of the obtained derivatives was subjected to gas chromatographic analysis using an ECNSS-M coated column (Gaschrom Q mfd. by Wako Pure Chemical Co. Ltd.). In the case of the polysaccharide in the present invention, there are consequently detected the same compounds as the ones obtained when L-rhamnose, D-galactose and D-glucose are treated individually. By comparing the ratios of the compounds obtained when treating the said polysaccharide and the modified one in which the carboxyl group as an uronic acid residue is reduced, it is possible to determine the component sugars of the polysaccharide and their molar ratios.

Now, a process for preparation of the polysaccharide used for the immunoactivating agent of the present invention is described.

Usually the said polysaccharide is obtained from the microbial culture of *Klebsiella oxytoca* TNM-3 strain disclosed in Japanese Patent Application No. 7-93100 (deposited under FERM BP-4669 at Life Science and Engineering Research Institute of the Agency of Industrial Science and Technology, the Ministry of International Trade and Industry, at 1-1-3, Higashi, Tsukuba-shi, Ibaraki-ken, Japan 305, received on May 18, 1994) or a variant thereof, or Klebsiella K19 strain disclosed in Carbohydrate Research, Vol. 157, pp. 13–25, 1986. All restrictions upon availability of the deposit of the microbial culture of *Klebsiella oxytoca* TNM-3 strain will be irrevocably removed upon granting of a patent on the above-identified application.

The said variant can be generated by exposure to radiation such as ultraviolet rays or X-rays, or by a known mutagenic means, for example, introduction of a chemical mutagen such as ethylmethanesulfonic acid (EMS) and/or N-methyl-N'-nitro-N-nitrosoguanidine (MNNG).

Microbial culture using *Klebsiella oxytoca* TNM-3 strain is described in Japanese Patent Application No. 7-93100. The microbial culture using the said strain, of the polysaccharide in the present invention is described as follows.

The medium used for the microbial culture is not specifically limited as far as it is capable of growing the microorganisms of the genius Klebsiella and the pertinent amounts of a carbon source, a nitrogen source, an inorganic salt and micronutrients are contaied for producing the said polysaccharide.

The carbon sources usable in the present invention include glucose, lactose, maltose, xylose, mannitol, saccharose, rhamnose, arabinose, trehalose, raffinose and the like.

The nitrogen sources include synthetic compounds such as nitrates, ammonium salts and urea, and natural organic matters such as polypeptone, corn steep liquor, yeast extract, meat extract, defatted soybean extract, peptide and amino acids. The inorganic salts usable as medium ingredient include phosphates, potassium salts, sulfates and magnesium salts. As micronutrients, yeast extract, various kinds of vitamins and such can be used. If necessary, other materials such as iron salt, calcium salt, manganese salt, etc., may be added to the medium.

The state of the medium may be either solid or liquid. In case of using a liquid medium, although stationary culture may be used, it is preferable to adopt shaking culture or aerated spinner culture because of higher yield of the objective polysaccharide. The incubation pH is not specifically defined as far as it allows growth of the microorganism and production of the objective polysaccharide, but usually it is preferable to set the pH at 4 to 8. The incubation temperature is also not specified in this invention, but normally a temperature of 20° to 35° C. is preferable. As for the incubation time, a period which maximizes the production of the objective polysaccharide should be chosen, but usually a period of 1 to 7 days is preferable.

Known methods can be employed for collecting the objective polysaccharide from the culture. For instance, the microbial cells are first removed from the culture by suitable means such as centrifugation or filtration, and then an organic solvent such as methanol, ethanol, isopropanol, acetone or the like is added to the obtained culture solution to produce a precipitate. The collected precipitate is dissolved in water and then dialyzed against water, and the dialyzate is dried by suitable means such as drafting, hot-air drying, spray drying, drum drying, vacuum drying, freeze drying, etc., to recover the objective polysaccharide.

In another method, the components other than the polysaccharide are removed from the culture by ultrafiltration, and the obtained concentrated solution is subjected to the said drying operation. Further, if necessary, the obtained polysaccharide may be purified by an ordinary polysaccharide purification method to obtain a high-purity product. As purification method, there can be used various kinds of column chromatography such as ion exchange, gel filtration and affinity, precipitation or salting-out by use of a quaternary ammonium salt, and precipitation by use of an organic solvent.

The degree of polymerization of the polysaccharide in the present invention can be changed by adjusting the preparation conditions such as culture medium composition and culture collecting method. Also, the collected or purified product may be hydrolyzed by using TFA, formic acid, hydrochloric acid or the like and adjusting the operating conditions. A preferable result can also be obtained by changing the degree of polymerization by performing heating under pressure or ultrasonic treatment. Therefore, the molecular weight of the said polysaccharide can be optionally set within the range of approximately $1 \times 10^3$ to $10 \times 10^6$. The thus obtained polysaccharide has an immunoactivating potency as shown in the Examples described later and its yield is higher than 50% on the average based on glucose used as a starting material. Further, in an oral acute toxicity test of the said polysaccharide on rats, no case of death was observed even when the rats were dosed with 5 g/kg of the polysaccharide. Also, the increase of body weight of the rats in the test group was the same as that of the control group, and absolutely no abnormality was seen in both appearance and postmortem anatomical examinations.

From the above, it is apparent that the said polysaccharides have a high safety. This fact is further supported by the comparison with $LD_{50}$ value of the commercial chemical therapeutic agents for cancer shown below.

$LD_{50}$ (mg/kg) of commercial chemical therapeutic agents for cancer in oral administration to rats (Values given in "Therapeutical Agents: A Collection of Japan Pharmaceutical Preparations, 9th Ed. (1985), compiled by Japan Medical Information Center" (pub. by Yakuji Jiho-sha))

| | |
|---|---|
| Cyclophosphide | 100 (male), 118 (female) |
| Cisplatin | 34.3 (male), 36.6 (female) |
| Mitomycin C | 67.4 |
| Fluorouracil | 781 |
| Carboquone | 27.3 |

Best Embodiment for Practice of the Invention

The present invention is described in more detail below by the following examples, but it should be understood that these examples are merely intended to be illustrative and not to be construed as limiting the scope of the invention.

Polysaccharide Preparation Example 1

First, 100 ml of a medium of the composition shown in Table 1 was put into a 500 ml Sakaguchi flask, and after moist heat sterilization at 120° C. for 20 minutes, a platinum loopful of *Klebsiella oxytoca* TNM-3 strain (FERM BP-4669) which had been under liquid shaking culture in a test tube using a medium of the composition shown in Table 2 for 3 days was inoculated in the first-said medium and subjected to reciprocal shaking culture at a shaking frequency of 110 strokes per minute at 28° C. for one day.

TABLE 1

Medium composition (wt %)

| | |
|---|---|
| Glucose | 2% |
| Polypeptone | 0.1% |
| Potassium monohydrogenphosphate | 0.15% |
| Magnesium sulfate heptahydrate | 0.05% |
| Vitamin B1 | 0.0005% |
| Biotin | 0.000006 |
| Calcium pantothenate | 0.001% |
| Nicotineamide | 0.0005% |
| pH | 6.5 |

Then, 400 ml of the resulting culture was inoculated in 8 liters of a medium of the composition shown in Table 2 contained in a 15-liter jar fermentor and sterilized in the same way as described above, and was subjected to 95-hour aerated spinner culture at 28° C. and an aeration rate of 5 l/min using a 5M sodium hydroxide solution while maintaining the pH of the system at 7. The spinner speed was 200 r.p.m. in the period from start till the 24th hour of incubation, 400 r.p.m. in the succeeding 25th to 33rd hour period and 700 r.p.m. in the period thereafter till the end (95th hour) of incubation.

TABLE 2

Medium composition (wt %)

| | |
|---|---|
| Glucose | 4% |
| Polypeptone | 0.2% |
| Potassium monohydrogenphosphate | 0.15% |
| Magnesium sulfate heptahydrate | 0.01% |
| Vitamin B1 | 0.0005% |
| Biotin | 0.000006% |
| Calcium pantothenate | 0.001% |
| Nicotineamide | 0.0005% |

The resulting culture was adjusted to pH 4.5 with 10% sulfuric acid, then moist heat sterilized at 121° C. for 60 minutes and centrifuged to remove the microbial cells. The supernatant was subjected to cross-flow type ultrafiltration repeatedly until the substances other than the polysaccharide, such as residual medium components, have been removed. Ultrafiltration System "UF-LMSII" of Toso Corp. (fractional molecular weight: $3 \times 10^6$) was used for ultrafiltration. The concentrated solution which did not pass through the filter was freeze-dried to obtain approximately 21 g of a single polysaccharide per liter of the medium (a yield of slightly greater than 50% of starting glucose). Singleness of the polysaccharide was confirmed by GPC-mode high performance liquid chromatography.

The molecular weight of the said polysaccharide was determined by high performance liquid chromatography using a column "Asahipak GFA-7MF" (Asahi Chemical Industry Co., Ltd.) with a 0.1M sodium nitrate solution as mobile phase. From the chromatographic peak top retention time of the polysaccharide, the molecular weight of the obtained polysaccharide was approximately $1.5 \times 10^6$ by use of the molecular weight-retention time standard curve drawn up using pullulan of the known molecular weight as standard.

The said polysaccharide and the modified one in which the carboxyl group of the glucuronic acid residue had been reduced were hydrolyzed down to the component saccharides to prepare the corresponding aditol acetates and then subjected to a gas chromatographic analysis. The molar ratio of the component sugars as determined from the previously prepared calibration curves and the peak areas of the respective component sugars is D-glucuronic acid:L-rhamnose:D-galactose:D-glucose=1:3:1:1.

Polysaccharide Preparation Example 2

The same procedure as in Preparation Example 1 was conducted except that the moist heat sterilization time for the culture after aerated spinner culture was changed from 60 minutes to 100 minutes, and that the fractional molecular weight of the system using ultrafiltration was set at $1 \times 10^5$ to obtain a polysaccharide. The molar ratio of the component sugars of the obtained polysaccharide, determined in the same way as in Example 1, is as follows: D-glucuronic acid:L-rhamnose:D-galactose D-glucose=1:2.8:1:1 . The molecular weight of the obtained polysaccharide was $2 \times 10^5$.

Polysaccharide Preparation Example 3

Reciprocal shaking culture was carried out according to Preparation Example 1 to obtain a culture fluid.

Then, 400 ml of this culture fluid was inoculated in 6 liters of a medium of the composition shown in Table 3 contained in a 10-liter jar fermentor and sterilized in the same way as in Preparation Example 1, and was subjected to 86-hour aerated spinner culture at 28° C. and an aeration rate of 3.6 l/min until the 21st hour of incubation and 4.8 l/min for the rest of incubation period while maintaining pH in the system at 7 by using a 5M sodium hydroxide solution. The spinner speed was 250 r.p.m. till the 20th hour of incubation, 500 r.p.m. in the succeeding period till the 36th hour of incubation and 650 r.p.m. in the period thereafter till the end (86th hour) of incubation.

TABLE 3

Medium composition (wt %)

| | |
|---|---|
| Glucose | 2% |
| Ammonium sulfate | 0.06% |
| Potassium monohydrogenphosphate | 0.15% |
| Magnesium sulfate heptahydrate | 0.05% |
| Iron sulfate heptahydrate | 0.003% |
| Disodium ethylenediaminetetracetate dehydrate | 0.01% |

TABLE 3-continued

| Medium composition (wt %) | |
|---|---|
| Vitamin B1 | 0.0005% |
| Biotin | 0.000006% |
| Calcium pantothenate | 0.001% |
| Nicotinamide | 0.0005% |

The resulting culture was moist heat sterilized at 121° C. for 20 minutes and then centrifuged to remove the microbial cells. The supernatant was subjected to cross-flow ultrafiltration repeatedly until the substances other than the polysaccharide, such as residual medium components have been eliminated. Toso Ultrafiltration System "UF-LMSII" (fractional molecular weight: $1 \times 10^5$) was used for ultrafiltration. The concentrated solution which did not pass through the filter was freeze-dried to obtain 9.6 g of a single polysaccharide per liter of the medium. Singleness of the polysaccharide was confirmed by using GPC-mode high performance liquid chromatography.

The molecular weight of the obtained polysaccharide and the molar ratios of the component sugars were determined in the same way as in Preparation Example 1. The molecular weight was approximately $3.2 \times 10^5$, and the molar ratio of the component sugars is D-glucuronic acid:L-rhamnose:D-galactose D-glucose=0.9:2.8 : 1.0:1.1.

Preparation of Polysaccharide for Measuring Immunoactivating Potency

First, 1 wt % aqueous solutions of the respective polysaccharides obtained in the above Preparation Examples were prepared. A cationic ion exchange resin was added to each solution to convert the counter ions of carboxyl group of glucuronic acid residue in the polysaccharide into hydrogen ions, and then the solution was neutralized with sodium hydroxide to replace the counter ions with sodium ions, then passed through a 0.2 μm-opening membrane filter and freeze-dried. The resulting polysaccharide preparations were subjected to the following tests.

EXAMPLE 1

(Determination of Cancer Growth Inhibitory Effect)

Five ICR mice (male, 5-week-old), in which Sarcoma 180 cancer cells ($5 \times 10^6$) had been subcutaneous-grafted, were prepared for each reagent to be tested. The polysaccharides obtained in Preparation Examples 1 and 2 were administered interperitoneally to the mice at a dose of 30 mg/kg per day continuously for 10 days, starting 24 hours after cancer cell grafting. After 5 weeks from cancer cell grafting, the weight of the solid cancer in each mouse was measured and the cancer cell growth inhibition rate was determined from the average of measurements of the five mice tested. The same test was conducted with lentinan.

The cancer cell growth inhibition percentage (%) was calculated from the following equation:

$$\text{Cancer cell growth inhibition percentage} = \frac{W_1 - W_2}{W_1} \times 100$$

$W_1$: average weight of the solid cancers in the 5 cancer cell grafted mice to which no reagent has been administered;

$W_2$: average weight of the solid cancers in case a reagent such as polysaccharide has been administered to the mice.

The results are shown in Table 4. A greater numerical value of inhibition percentage indicates a greater potency to control growth of the cancer cells.

TABLE 4

| | Cancer cell growth inhibition percentage (%) |
|---|---|
| Mice to which the polysaccharide obtained in Preparation Example 1 was administered. | 98 |
| Mice to which the polysaccharide obtained in Preparation Example 2 was administered. | 89 |
| Lentinan | 100 |

A polysaccharic substance A29-PS disclosed in Japanese Patent Publication (KOKOKU) No. 1-59283, which is an acidic heteropolysaccharide like the polysaccharide in the present invention, showed a cancer cell growth inhibition percentage of approximately 30% in the same test as conducted in Example 1 described above.

From the above results, the polysaccharides in the present invention have an excellent immunoactivating potency.

EXAMPLE 2

(Determination of Cytotoxic T Cell (CTL) Inducibility)

The following test was conducted on the C3H mice and BALB/c mice which are different in H-2 haplotype.

The spleen lymphocytes ($2 \times 10^7$) of the BALB/c mice were immunized in the abdominal cavities of the C3H mice (4 mice per group: N=4). Each of the test specimens shown in Table 5 was given subcutaneously to the back of each of the said C3H mice at a dose of 50 mg/kg or 20 mg/kg, once a day, four times in all, from the day before immunization till 2 days after immunization. As control, physiological saline was used instead of the test specimens. After 9 days, the spleen lymphocyte suspension was collected from the C3H mice. This lymphocyte suspension contained the cytotoxic T cells (hereinafter referred to as effector cells and abbreviated as E). Then, $10^4$ cells of myeloma cell strain NS-1/Z (hereinafter abbreviated as T) derived from the BALB/c mouse into which β-galactosidase (β-gal) of *Escherichia coli* had been introduced, were mixed as target cells with the effector cells so that the E/T ratio would become 30, 60 or 120, and the mixture was kept in 0.2 ml of a medium RPMI-1640 at 37° C. for 4 hours. The activity of β-gal released into the supernatant by destruction of the target cells was measured, and the cytotoxicity by CTL was calculated from the following equation. The immunoactivating activity is shown in Table 5.

$$\text{Cytotoxicity (\%)} = \frac{A - B}{C - B} \times 100$$

A: released β-gal activity

B: naturally released β-gal activity (enzyme release observed when no effector cells are present)

C: overall β-gal activity (T used is dissolved in 0.0425% Triton-X100 and the overall enzyme activity is measured.)

$$\text{Immunoactivating activity} = \frac{\text{cytotoxity (\%) in case where a test specimen was administrated}}{\text{cytotoxity (\%) in case where a physiological saline was administrated}}$$

TABLE 5

| Specimen | Dosage (mg/kg/day) | Immunoactivating activity | | |
|---|---|---|---|---|
| | | E/T = 30 | E/T = 60 | E/T = 120 |
| Polysaccharide obtained in Preparation Example 1 | 50 | 2.4 | 2.1 | 2.5 |
| Polysaccharide obtained in Preparation Example 3 | 50 | 1.4 | 1.3 | 1.5 |
| Schizophyllan | 20 | 5.5 | 2.0 | 1.7 |

EXAMPLE 3

(Measurement of Tumor Necrosis Factor (TNF) Interleukin (IL-6) Inducibility)

First, 100 μg/0.2 ml of MDP (N-acetylmuramyl-L-alanyl-D-isoglutamine) was injected intravenously to the C3H/He mice (6- to 12-week-old) in groups of three, and 4 hours later, the polysaccharide obtained in Preparation Example 3 (hereinafter called polysaccharide A), the polysaccharide in which carboxyl group in glucuronic acid residue has been reduced according to the Tayler et al. method (Biochemistry, Vol. 11, No. 8, 1383-1388, 1972) (this polysaccharide being hereinafter called polysaccharide B) and schizophyllan which is a commercial polysaccharide having immunoactivating potency (produced by Taito Co., Ltd. and sold by Kaken Pharmaceutical Co., Ltd.), were injected intravenously at a dose of 100 μg/0.2 ml. These mice were left under observation for anaphylaxis-like reaction and sudden death. After 90 minutes from the injection, blood was collected from the surviving mice to determine TNF and IL-6 activities in the serum. TNF activity was calculated on the basis of the ratio of activity of the actinomycin D-treated L-929 cells to that of rHuTNF (human recombination TNF) used as control, with the killing action of the said L-929 cells being taken as index, and indicated by ng/ml. In the case of IL-6 activity, the IL-6 dependent MH60.BSF2 cell growth stimulating action was taken as index, and the IL-6 activity was calculated on the basis of the calibration curves obtained from the test of IL-6 and control rHuIL-6, and indicated by U/ml. The results represented by average value ± standard deviation are shown in Table 6.

TABLE 6

| | Anaphylaxis-like reaction | Sudden death | TNF (ng/ml) | IL-6 (U/ml) |
|---|---|---|---|---|
| Polysaccharide A | 0/3 | 0/3 | 507.0 ± 136.5 | 825.0 ± 588.4 |
| Polysaccharide B | 0/3 | 0/3 | 312.0 ± 45.0 | 731.7 ± 342.2 |
| Schizophyllan | 0/3 | 0/3 | 0 ± 0 | 14.1 ± 2.2 |

As is seen from the above table, the polysaccharides in the present invention have a TNF and IL-6 inducibility which is not possessed by schizophyllan.

As described above, according to the present invention, there can be provided an immunoactivating agent having a prominent effect with higher productivity than the polysaccharides derived from basidiomycetes such as krestin and lentinan. According to the present invention, there is also provided an immunoactivating agent whose toxicity is very low as compared with the conventional chemical therapeutical agents for cancer and which has the functions not observed with schizophyllan which is known to have an immunoactivating potency. Therefore, the immunoactivating agent of the present invention is expected to be applicable to prevention and treatment of cancer, prevention and treatment of microbial or viral infections, recovery of postoperative reduction of immunity and like uses.

What is claimed is:

1. An immunoactivating polysaccharide consisting essentially of glucuronic acid, rhamnose, galactose and glucose in a molar ratio of glucuronic acid:L-rhamnose:galactose:glucose=0 to 1.2:2.4 to 3.6:0.8 to 1.2:0.8 to 2.4.

2. An immunoactivating polysaccharide according to claim 1, wherein the molar ratio of the constituting sugars is glucuronic acid:rhamnose:galactose:glucose=0.8 to 1.2:2.4 to 3.6:0.8 to 1.2:0.8 to 1.2.

3. An immunoactivating polysaccharide according to claim 1 wherein the molecular weight of the polysaccharide measured by gel filtration chromatography is approximately $1 \times 10^3$ to $10 \times 10^6$.

4. An immunoactivating polysaccharide according to claim 1, wherein the bonding form of the constituting sugars is as follows:

bonding form of rhamnose: (1→2) bond and (1→bond)

(the constituting ratio of the above bonds being (1→2) (1→bond)=1.3 to 3.0:1);

bonding form of glucuronic acid: (1→3) bond and (1→4) bond;

bonding form of galactose: (1→3) bond;

bonding form of glucose: (1→2) bond.

5. An immunoactivating polysaccharide according to claim 1, wherein the bonding configuration of rhamnose, glucuronic acid and glucose is α, and the bonding configuration of galactose is β.

6. An immunoactivating polysaccharide according to claim 1, wherein the main bonding form and the molar ratio of the constituting sugars is as follows:

L-Rha-(1 —→ :2 —→ )L-Rha(1 —→ :3 —→ )

D-Gal(1 —→ :2 —→ )D-Glc(1 —→ :3 —→ )

D-GlcUA(1 —→
4
↑

= 0.8 to 1.2:1.6 to 2.4:0.8 to 1.2:0.8 to 1.2:0.8 to 1.2.

(wherein Rha, Gal, Glc and GlcUA represent rhamnose, galactose, glucose and glucuronic acid, respectively, and the numerical figures indicate the positions of glucoside bonds).

* * * * *